United States Patent [19]

Sirrenberg et al.

[11] 4,194,005
[45] Mar. 18, 1980

[54] COMBATING ARTHROPODS WITH 4-CYANO-4'-[N-(N'-SUBSTITUTED-BENZOYL)-UREIDO]-DIPHENYL ETHERS

[75] Inventors: Wilhelm Sirrenberg, Sprockhoevel; Erich Klauke, Cologne; Jürgen Schramm, Dormagen; Ingeborg Hammann, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 819,631

[22] Filed: Jul. 27, 1977

[30] Foreign Application Priority Data

Aug. 25, 1976 [DE] Fed. Rep. of Germany ....... 2638233

[51] Int. Cl.$^2$ .................... A01N 9/20; C07C 121/78
[52] U.S. Cl. .................... 424/304; 260/465 D; 260/465 E; 260/465 F
[58] Field of Search .................... 260/465 D; 424/304

[56] References Cited

U.S. PATENT DOCUMENTS

| 3,992,553 | 11/1976 | Sirrenberg et al. .................. 424/304 |
| 4,064,267 | 12/1977 | Sirrenberg et al. .................. 424/304 |

*Primary Examiner*—Dolph H. Torrence
*Attorney, Agent, or Firm*—Sprung, Felfe, Horn, Lynch & Kramer

[57] ABSTRACT

4-Cyano-4'-[N-(N'-substituted-benzoyl)-ureido]-diphenyl ethers of the formula

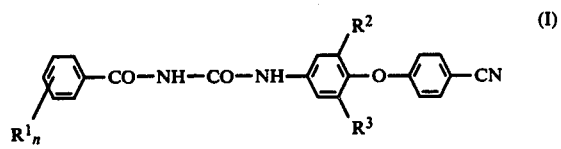

in which
$R^1$ represents halogen or alkyl,
$R^2$ represents chlorine, bromine or hydrogen,
$R^3$ represents bromine or hydrogen, and
n represents 1, 2, 3, 4 or 5,
which possess arthropodicidal properties.

10 Claims, No Drawings

COMBATING ARTHROPODS WITH 4-CYANO-4'-[N-(N'-SUBSTITUTED-BENZOYL)-UREIDO]-DIPHENYL ETHERS

The present invention relates to and has for its objects the provision of particular new 4-cyano-4'-[N-(N'-substituted-benzoyl)-ureido]-diphenyl ethers which possess arthropodicidal properties, active compositions in the form of mixtures of such compounds with solid and liquid dispersible carrier vehicles, and methods for producing such compounds and for using such compounds in a new way especially for combating pests, e.g. insects, with other and further objects becoming apparent from a study of the within specification and accompanying examples.

It is known from German Published Specification DOS 2,123,236 that certain benzoylureas, for example 1-[4-chloro-(Compound A) and 3,4-dichloro-phenyl]-3-[2,6-dichlorobenzoyl]-urea (Compound B), possess insecticidal properties.

The present invention now provides, as new compounds, the substituted benzoylureidodiphenyl ethers of the general formula

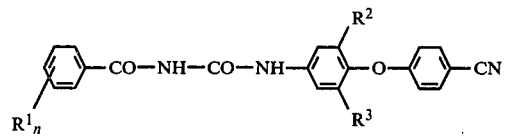

in which
R$^1$ represents halogen or alkyl,
R$^2$ represents chlorine, bromine or hydrogen,
R$^3$ represents bromine or hydrogen, and
n represents 1, 2, 3, 4 or 5.

Preferably, R$^1$ represents fluorine, chlorine, bromine, iodine or straight-chain or branched alkyl with 1 to 4 (especially 1 or 2) carbon atoms and n represents 1, 2 or 3.

Surprisingly, the substituted benzoylureidodiphenyl ethers according to the invention possess a substantially better insecticidal action than the benzoylureas of analogous structure, and of the same type of action, previously known from the state of the art. The compounds according to the invention thus represent a genuine enrichment of the art.

The invention also provides a process for the preparation of a substituted benzoylureidodiphenyl ether of the formula (I), in which (a) a phenoxyaniline of the general formula

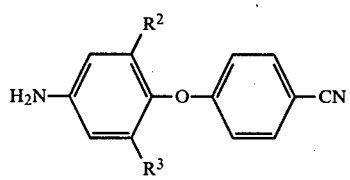

is reacted with a benzoyl isocyanate of the general formula

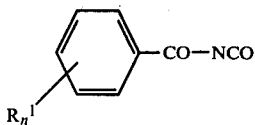

in which formulae
R$^1$, R$^2$, R$^3$ and n have the above-mentioned meanings, if appropriate in the presence of a diluent, or (b) a 4-isocyanato-diphenyl ether of the general formula

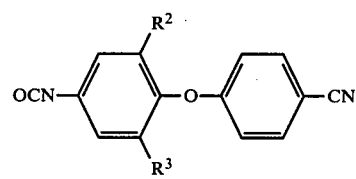

is reacted with a benzamide of the general formula

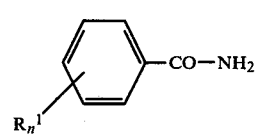

in which formulae
R$^1$, R$^2$, R$^3$ and n have the above-mentioned meanings, if appropriate in the presence of a diluent.

If, using process variant (a), 4-(4-cyanophenoxy)-3-bromo-5-chloroaniline and 2-ethyl-benzoyl isocyanate are used as starting materials and, using process variant (b), 4-(4-cyanophenoxy)-3,5-dibromo phenyl isocyanate and 2-ethylbenzamide are used as starting materials, the course of the reaction can be represented by the following equations:

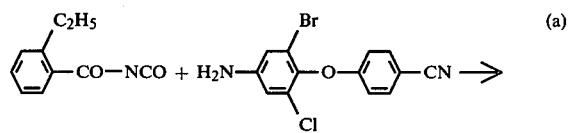

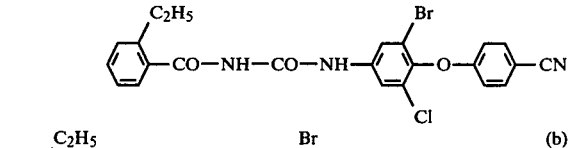

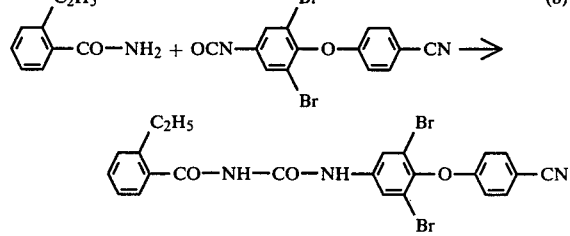

The phenoxyanilines (II) to be used as starting materials can be prepared in accordance with processes known from the literature [see Liebigs Annalen 710, pages 169–179 (1970)] or by, for example, reacting 4-chloro-benzonitrile with 4-aminophenolates or reacting 4-cyanophenolates with 1-chloro-4-nitrobenzene derivatives to give the corresponding nitro compound, which is then converted by reduction to the amino compound, from which the corresponding 4-isocyanatodiphenyl ethers (IV) may be obtained by reaction with phosgene.

The following may be mentioned as individual examples of the phenoxyanilines (II) and of the 4-isocyanatodiphenyl ethers (IV): 3,5-dibromo-, 3-chloro-, 3-bromo- and 3-bromo-5chloro-4-(4-cyanophenoxy)-aniline, 4-(4-cyanophenoxy)-aniline and the corresponding isocyanate compounds.

The benzoyl isocyanates (III) also to be used as starting materials are known and can be prepared in accordance with generally customary processes [see A. J. Speziale et al., J. Org. Chem. 30 (12), page 4306–4307 (1965)].

The following may be mentioned as individual examples of these compounds: 2-fluoro-, 2-chloro-, 2-bromo-, 2-iodo-, 2-methyl-, 2-ethyl-, 2,6-difluoro-, 2,6-dichloro-, 2,6-dibromo- and 2,6-diiodo-benzoyl isocyanate.

Furthermore, the benzamides (V) required as starting materials are also known and can be prepared in accordance with generally customary methods [see Beilstein's "Handbuch der organischen Chemie" ("Handbook of Organic Chemistry"), volume 9, page 336].

The following may be mentioned as individual examples of these compounds: 2-fluoro-, 2-chloro-, 2-bromo-, 2-iodo-, 2-methyl-, 2-ethyl-, 2,6-difluoro-, 2,6-dichloro-, 2,6-dibromo- and 2,6-diiodo-benzamide.

The process variants for the preparation of the compounds according to the invention are preferably carried out in the presence of a suitable diluent, which term herein includes a solvent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

The reaction temperature in either process variant can be varied within a substantial range. In general, the reaction is carried out at from 0° to 120° C., preferably at from 40° to 80° C.

The reaction is in general allowed to take place under normal pressure.

To carry out the process, the starting compounds are in most cases employed in stoichiometric amounts. An excess of one or other reactant produces no significant advantages. The reactants are in most cases brought together in one of the above-mentioned solvents and are in most cases stirred at an elevated temperature for one or more hours in order to complete the reaction, and the product which separates out is isolated by filtration, washing or drying and, if appropriate, recrystallizing. The compounds are obtained in a crystalline form and are characterized by melting point.

The active compounds are well tolerated by plants, have a favorable level of toxicity to warm-blooded animals, and can be used for combating arthropod pests, especially insects, which are encountered in agriculture, in forestry, in the protection of stored products and of materials, and in the hygiene field. They are active against normally sensitive and resistant species and against all or some stages of development. The above-mentioned pests include: from the class of the Isopoda, for example *Onsicus asellus, Armadillidium vulgare* and *Porcellio scaber;* from the class of the Diplopoda, for example *Blaniulus guttulatus;* from the class of the Chilopoda, for example *Geophilus carpophagus* and *Scutigera spec.;* from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea moderae, Blattella germanica, Acheta domesticus, Gryllotalpa spp., Locusta migratoria migratorioides, Melanoplus differentialis* and *Schistocerca gregaria;* from the order of the Dermaptera, for example *Forficula auricularia;* from the order of the Isoptera, for example *Reticulitermes spp.;* from the order of the Anoplura, for example *Phylloxera vastratrix, Pemphigus spp., Pediculus humanus corporis, Haematopinus spp.* and *Linognathus spp.;* from the order of the Mallophaga, for example *Trichodectes spp.* and *Damalinea spp.;* from the order of the Thysanoptera, for example *Hercinothrips femoralis* and *Thrips tabaci;* from the order of the Heteroptera, for example *Eurygaster spp., Dysdercus intermedius, Piesma quadrata, Cimex lectularius, Rhodnius prolixus* and *Triatoma spp.;* from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp.* and *Psylla spp.;* from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Barias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica;* from the order of the Hymenoptera, for example *Diprion spp., Hoplocampa spp.,* Lasius spp., *Monomorium pharaonis* and *Vespa spp.;* from the order of the Diptera, for example *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp, Stomoxys spp., Oestrus spp., Hypoderma spp., Tabanus spp., Tannia spp., Bibio*

*hortulanus, Oscinella frit, Phorbia spp., Pegomyia hyoscyami, Ceratitis capitata, Dacus oleae* and *Tipula paludosa;* from the order of the Siphonaptera, for example *Xenopsylla cheopis* and *Ceratophyllus spp.;* from the class of the Arachnida, for example *Scorpio maurus* and *Latrodectus mactans;* from the order of the Acarina, for example, *Acarus siro, Argas spp., Ornithodorus spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp.* and *Tetranychus spp.*.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichlorofluoromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl aryl-polyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carried liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. and insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test

Solvent: 3 parts by weight of dimethylformamide

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (Brassica oleracea) were sprayed with the preparation of the active compound until dew moist and were then infested with caterpillars of the diamond-back moth (Plutella maculipennis).

After the specified periods of time, the degree of destruction was determined as a percentage: 100% meant that all the caterpillars were killed whereas 0% meant that none of the caterpillars were killed.

The active compounds, the concentrations of the active compounds, the evaluation times and the results can be seen from the following table:

Table 1

(Insects which damage plants)
*Plutella* test

| Active compounds | | Active compound concentration in % | Degree of destruction in % after 7 days |
|---|---|---|---|
| 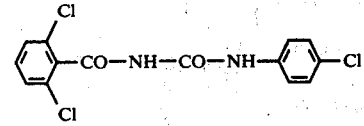 (known) | (A) | 0.1<br>0.01 | 65<br>0 |
| 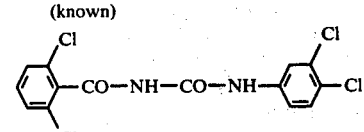 (known) | (B) | 0.1<br>0.01<br>0.001 | 100<br>100<br>0 |
| 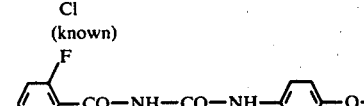 | (2) | 0.1<br>0.01<br>0.001 | 100<br>100<br>100 |
| 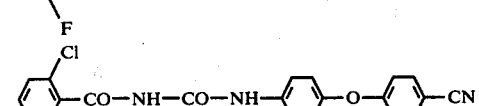 | (3) | 0.1<br>0.01<br>0.001 | 100<br>100<br>100 |
| 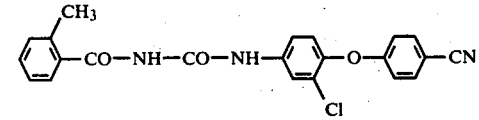 | (4) | 0.1<br>0.01<br>0.001 | 100<br>100<br>100 |
| 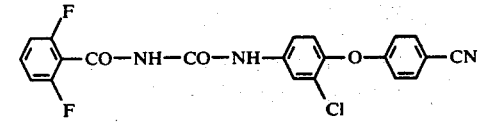 | (6) | 0.1<br>0.01<br>0.001 | 100<br>100<br>100 |
| 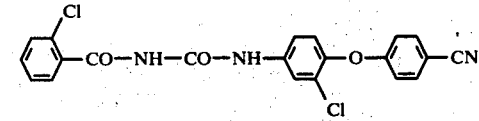 | (1) | 0.1<br>0.01<br>0.001 | 100<br>100<br>100 |

Table 1-continued (Insects which damage plants)
Plutella test

| Active compounds | | Active compound concentration in % | Degree of destruction in % after 7 days |
|---|---|---|---|
| 2-Br-C6H4-CO-NH-CO-NH-C6H3(Cl)-O-C6H4-CN | (7) | 0.1<br>0.01<br>0.001 | 100<br>100<br>100 |
| 2-Cl-C6H4-CO-NH-CO-NH-C6H3(Br)-O-C6H4-CN | (8) | 0.1<br>0.01<br>0.001 | 100<br>100<br>100 |
| 2,6-F2-C6H3-CO-NH-CO-NH-C6H3(Br)-O-C6H4-CN | (16) | 0.1<br>0.01<br>0.001 | 100<br>100<br>100 |
| 2-Cl-C6H4-CO-NH-CO-NH-C6H3(Br)-O-C6H4-CN | (15) | 0.1<br>0.01<br>0.001 | 100<br>100<br>100 |
| 2-F-C6H4-CO-NH-CO-NH-C6H3(Br)(Cl)-O-C6H4-CN | (14) | 0.1<br>0.01<br>0.001 | 100<br>100<br>100 |
| 2,6-F2-C6H3-CO-NH-CO-NH-C6H3(Br)(Cl)-O-C6H4-CN | (13) | 0.1<br>0.01<br>0.001 | 100<br>100<br>100 |
| 2-Cl-C6H4-CO-NH-CO-NH-C6H3(Br)(Cl)-O-C6H4-CN | (20) | 0.1<br>0.01<br>0.001 | 100<br>100<br>100 |
| 2-Br-C6H4-CO-NH-CO-NH-C6H3(Br)(Cl)-O-C6H4-CN | (17) | 0.1<br>0.01<br>0.001 | 100<br>100<br>100 |

EXAMPLE 2

Test with parasitic fly larvae

Solvent: 35 parts by weight of ethylene polyglycol monomethyl ether

Emulsifier: 35 parts by weight of nonylphenol polyglycol ether

To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (*Lucilia cuprina*) were introduced into a test tube which contained approximately 2 cm³ of horse muscle. 0.5 ml of the preparation of active compound was applied to this horse meat. After 24 hours, the degree of destruction in % was determined. 100% meant that all larvae had been killed and 0% meant that no larvae had been killed.

The active compounds, the concentrations of the active compounds and the results can be seen from the table which follows:

Table 2

| | (parasitic fly larvae/*Lucilia cuprina*) | | |
|---|---|---|---|
| Active compound | | Active compound concentration in ppm | Destruction action in % |
| 2-CH3-C6H4-CO-NH-CO-NH-C6H3(Cl)-O-C6H4-CN | (4) | 1,000<br>300<br>100 | >50<br>>50<br>0 |

Table 2-continued (parasitic fly larvae/*Lucilia cuprina*)

| Active compound | | Active compound concentration in ppm | Destruction action in % |
|---|---|---|---|
| 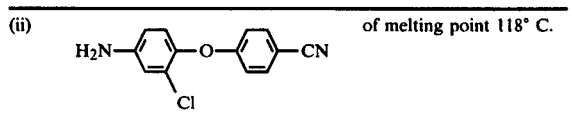 | (1) | 1,000<br>300<br>100<br>30 | 100<br>100<br><50<br>0 |
| 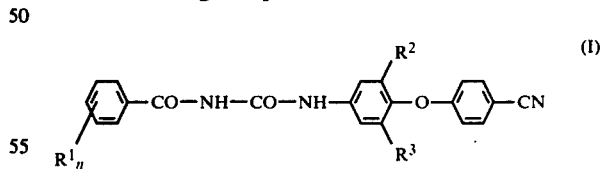 | (5) | 1,000<br>300 | 100<br>0 |

The process of the present invention is illustrated by the following preparative examples:

EXAMPLE 3

Some of the starting materials to be employed could be prepared as follows:

(a)

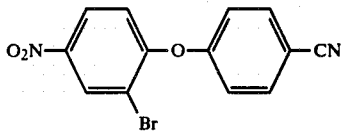

50 g (0.42 mol) of 4-hydroxybenzonitrile were dissolved in 300 ml of dimethylsulphoxide and a solution of 27 g of potassium hydroxide in 30 ml of water was added. 150 ml of distillate were stripped off in vacuo. 72 g (0.3 mol) of 3-bromo-4-chloro-1-nitrobenzene were added to the residue and the batch was heated for 1 hour at 80° C. and for a further hour at 100° C. After it had cooled, the product was precipitated by means of ice-water, while adding methanol, and was then filtered off. After washing with water and recrystallizing from ethanol, 63 g of the pure compound of melting point 115°–116° C. were obtained.

(b)

(i) 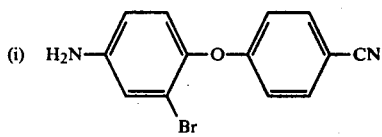

151 g (0.475 mol) of the 2-bromo-4-nitro-4'-cyanodiphenyl ether obtained under (a) were dissolved in 700 ml of ethanol and after adding 40 g of Raney nickel/iron and 10 g of sodium bicarbonate the compound was hydrogenated at 20° C. After completion of the hydrogenation, the solid products were filtered off and the filtrate was concentrated. The residue was recrystallized from benzene/ligroin and melted at 130°–105° C. The yield was 86 g (63% of theory).

The following compounds could be prepared analogously:

(ii) of melting point 118° C.

H₂N—⟨⟩—O—⟨⟩—CN
    |
    Cl (iii) of melting point 167° C.

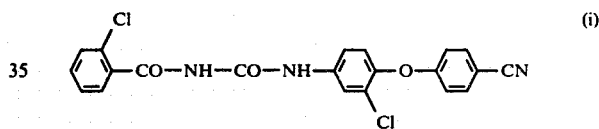

(iv) of melting point 166° C.

H₂N—⟨⟩—O—⟨⟩—CN
(with Br substituents)

EXAMPLE 4

(i)

Cl
|
⟨⟩—CO—NH—CO—NH—⟨⟩—O—⟨⟩—CN
                    |
                    Cl

A solution of 5.6 g (0.03 mol) of 2-chloro-benzoyl isocyanate in 20 ml of toluene was added dropwise, at 50° C., to 8.35 g (0.03 mol) of 3-chloro-4-(4-cyano-phenoxy)-aniline in 100 ml of toluene. The batch was stirred for 1 hour at 60° C. After it had cooled, the product which had precipitated was filtered off and washed first with toluene and then with petroleum ether. After drying, 10 g (78% of theory) of 4-cyano-2'-chloro-4'-[N-(N'-2-chlorobenzoyl)-ureido]-diphenyl ether of melting point 186° C. were obtained.

The following compounds of the formula (I)

$R^1_n$—⟨⟩—CO—NH—CO—NH—⟨⟩(R²)—O—⟨⟩—CN
                              |
                              R³ where synthesized analogously with no effort to optimize the yields:

| Compound No. | $R_n^1$ | $R^2$ | $R^3$ | Yield (% of theory) | Melting point (°C.) |
|---|---|---|---|---|---|
| 2 | 2,6-F | H | H | 85 | 233 |
| 3 | 2-Cl | H | H | 68 | 211 |
| 4 | 2-CH₃ | Cl | H | 74 | 177 |
| 5 | 2,6-Cl | Cl | H | 72 | 220 |
| 6 | 2,6-F | Cl | H | 94 | 218 |
| 7 | 2-Br | Cl | H | 63.5 | 206 |

-continued

| Compound No. | $R_n^1$ | $R^2$ | $R^3$ | Yield (% of theory) | Melting point (°C.) |
|---|---|---|---|---|---|
| 8 | 2-Cl | H | Br | 49.5 | 192 |
| 9 | 2,6-F | H | Br | 56 | 226 |
| 10 | 2-Br | H | Br | 84 | 194 |
| 11 | 2-CH₃ | H | Br | 51.5 | 206 |
| 12 | 2-Br | Cl | Br | 72.5 | 216 |
| 13 | 2,6-F | Cl | Br | 73 | 242 |
| 14 | 2-F | Cl | Br | 54.5 | 217 |
| 15 | 2-Cl | Br | Br | 42.5 | 205 |
| 16 | 2,6-F | Br | Br | 60.5 | 246 |
| 17 | 2-Br | Br | Br | 39 | 222 |
| 18 | 2-I | H | H | 82.5 | 197 |
| 19 | 2,6-Cl | Cl | Br | 49.5 | 247 |
| 20 | 2-Cl | Cl | Br | 33 | 206 |

It will be appreciated that the instant specification and examples are set forth by way of illustration and not limitation, and that various modifications and changes may be made without departing from the spirit and scope of the present invention.

What is claimed is:

1. A 4-cyano-4'-[N-(N'-substituted-benzoyl)-ureido]-diphenyl ether of the formula

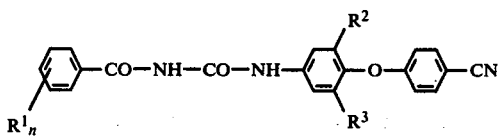

in which
R¹ is halogen or alkyl,
R² is chlorine, bromine or hydrogen,
R³ is bromine or hydrogen, and
n is 1, 2, 3, 4 or 5.

2. A compound according to claim 1, in which R¹ is fluorine, chlorine, bromine, iodine or alkyl with 1 to 4 carbon atoms, and n is 1, 2 or 3.

3. A compound according to claim 1 wherein such compound is 4-cyano-2'-chloro-4'-[N-(N'-2-chlorobenzoyl)-ureido]-diphenyl ether of the formula

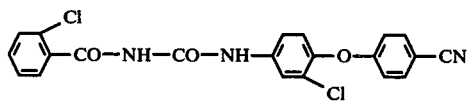

4. A compound according to claim 1 wherein such compound is 4-cyano-2'-bromo-6'-chloro-4'-[N-(N'-2-bromobenzoyl)-ureido]-diphenyl ether of the formula

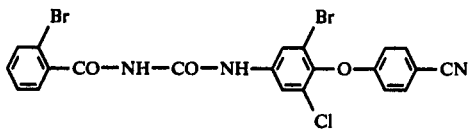

5. A compound according to claim 1 wherein such compound is 4-cyano-2'-bromo-6'-chloro-4'-[N-(N'-2,6-difluorobenzoyl)-ureido]-diphenyl ether of the formula

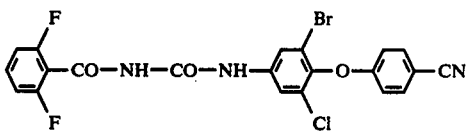

6. A compound according to claim 1 wherein such compound is 4-cyano-2',6'-dibromo-4'-[N-(N'-2-chlorobenzoyl)-ureido]-diphenyl ether of the formula

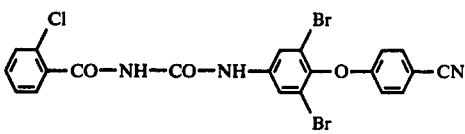

7. A compound according to claim 1 wherein such compound is 4-cyano-2'-bromo-6'chloro-4'-[N-(N'-2-chlorobenzoyl)-ureido]-diphenyl ether of the formula

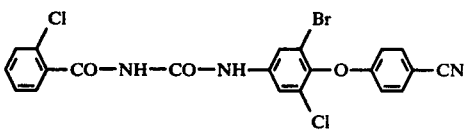

8. An arthropodicidal composition containing as active ingredient an arthropodicidally effective amount of a compound according to claim 1 in admixture with a diluent.

9. A method of combating arthropods which comprises applying to the arthropods, or to a habitat thereof, an arthropodicidally effective amount of a compound according to claim 1.

10. The method according to claim 9, in which said compound is
4-cyano-2'-chloro-4'-[N-(N'-2-chlorobenzoyl)-ureido]-diphenyl ether,
4-cyano-2'-bromo-6'-chloro-4'-[N-(N'-2-bromobenzoyl)-ureido]-diphenyl ether,
4-cyano-2'-bromo-6'-chloro-4'-[N-(N'-2,6-difluorobenzoyl)-ureido]-diphenyl ether,
4-cyano2',6'-dibromo-4'-[N-(N'-2-chlorobenzoyl)-ureido]-diphenyl ether, or
4-cyano-2'-bromo-6'-chloro-4'[N-(N'-2-chlorobenzoyl)-ureido]-diphenyl ether.

* * * * *